US005118443A

United States Patent [19]

Saito et al.

[11] Patent Number: 5,118,443

[45] Date of Patent: Jun. 2, 1992

[54] DEVELOPER FOR PRESSURE-SENSITIVE RECORDING SHEETS, AQUEOUS DISPERSION OF THE DEVELOPER AND METHOD FOR PREPARING THE DEVELOPER

[75] Inventors: Toranosuke Saito; Takashi Ishibashi, both of Osaka; Tomoharu Shiozaki, Hyogo; Tetsuo Shiraishi, Saitama, all of Japan

[73] Assignees: Sanko Kaihatsu Kagaku Kenkyusho, Osaka; Kanzaki Paper Manufacturing Co., Ltd., Tokyo, both of Japan

[21] Appl. No.: 644,678

[22] Filed: Jan. 22, 1991

Related U.S. Application Data

[63] Continuation of Ser. No. 277,321, Nov. 29, 1988, abandoned.

[30] Foreign Application Priority Data

Dec. 1, 1987 [JP] Japan ............................ 62-301510
Nov. 1, 1988 [JP] Japan ............................ 63-274555

[51] Int. Cl.[5] .................... B01J 13/00; C07C 65/10; B41M 5/155

[52] U.S. Cl. .............................. 252/311; 562/477; 503/225; 503/227

[58] Field of Search ............... 252/311; 503/200, 209, 503/212, 213, 216, 225

[56] References Cited

U.S. PATENT DOCUMENTS

| | | | |
|---|---|---|---|
| 3,983,292 | 9/1976 | Saito et al. | 503/212 |
| 4,046,941 | 9/1977 | Saito et al. | 503/225 X |
| 4,230,743 | 10/1980 | Nakamura et al. | 503/216 X |
| 4,749,680 | 6/1988 | Umeda et al. | 503/210 |
| 4,803,192 | 2/1989 | Saeki et al. | 503/212 |
| 4,806,521 | 2/1989 | Umeda et al. | 503/212 X |

FOREIGN PATENT DOCUMENTS

| | | | |
|---|---|---|---|
| 0219302 | 7/1986 | European Pat. Off. | 503/213 |
| 0233450 | 8/1987 | European Pat. Off. | |
| 0275107 | 1/1988 | European Pat. Off. | 503/213 |
| 2348639 | 4/1974 | Fed. Rep. of Germany | |
| 2151830 | 3/1973 | France | 503/213 |
| 2200785 | 4/1974 | France | 503/216 |
| 56-33985 | 6/1981 | Japan | 503/213 |
| 56-40583 | 6/1981 | Japan | 503/213 |
| 165868 | 9/1984 | Japan | 503/212 |
| 208985 | 9/1987 | Japan | 503/213 |
| 2030588 | 4/1980 | United Kingdom | 503/213 |
| 2034782 | 6/1980 | United Kingdom | 503/213 |
| 2172022 | 9/1986 | United Kingdom | 503/213 |

*Primary Examiner*—Richard D. Lovering
*Assistant Examiner*—John M. Covert
*Attorney, Agent, or Firm*—Baker & Daniels

[57] ABSTRACT

A developer comprising at least one polyvalent metal salt of a nuclear substituted salicylic acid of the following general formula is provided.

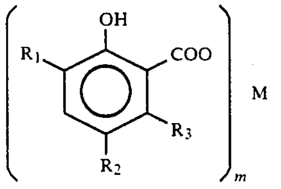

[I]

In the formula, $R_1$ represents an alkyl group having from 1 to 12 carbon atoms, $R_2$ represents a hydrogen atom or an alkyl group having from 1 to 12 carbon atoms, $R_3$ represents a hydrogen atom or a methyl group provided that at least one of $R_1$ and $R_2$ is a secondary butyl group, a secondary hexyl group, an isohexyl group, a secondary octyl group, an isononyl group, a secondary decyl group, a secondary dodecyl group or an isododecyl group and the total number of the carbon atoms in $R_1$, $R_2$ and $R_3$ is from 9 to 18, M is a polyvalent metal atom, and m is a valence of M. An aqueous dispersion containing the developer and a method for preparing the developer are also described.

5 Claims, 6 Drawing Sheets

DEVELOPER FOR PRESSURE-SENSITIVE RECORDING SHEETS, AQUEOUS DISPERSION OF THE DEVELOPER AND METHOD FOR PREPARING THE DEVELOPER

This is a continuation of application Ser. No. 07/277,321, filed Nov. 29, 1988, now abandoned.

BACKGROUND OF THE INVENTION

1. Field of the Invention

This invention relates to a developer for pressure-sensitive recording sheet, its aqueous dispersion, and a method for preparing the developer.

2. Description of Related Art

As described in U.S. Pat. Nos. 2,712,507, 2,800,457 and 3,418,250, pressure-sensitive recording sheets make use of combinations of electron donative colorless dye (hereinafter referred to simply as "dye") solutions encapsulated in microcapsules and electron acceptive compounds (hereinafter referred to simply as "developer"). When the microcapsules are broken by application of a pressure, the dye solution and the developer are contacted with each other and reacted to develop a color. In general, this type of sheet is called no carbon required paper and has widely been used.

The currently employed developers for the pressure-sensitive recording sheets include, aside from inorganic compounds such as activated clay, organic compounds such as formaldehyde polycondensates of para-substituted phenols, metal salts of nuclear substituted salicylic acids (Japanese Laid-open Patent Application Nos. 51-25174, 62-19486, 62-176875, 62-178387 and 62-178388). The present invention is concerned with metals salts of the nuclear substituted salicylic acids.

Most of polyvalent metal salts of nuclear substituted salicylic acids are insoluble in water and are superior as a developer to other developers with respect to the high color density and the stability in color image, thus being widely utilized. In general, these metal salts are resinous materials having high softening points. In most cases, they are divided into fine pieces and dispersed in water by means of pulverizers or mills such as a ball mill, an attritor, a sand grinder and the like. Subsequently, inorganic pigments, clay minerals, adhesives, dispersants and defoamers are added to the dispersion thereby preparing a coating composition, followed by coating and deposition on a substrate. Therefore, amorphous compounds of the polyvalent metal salts of nuclear substituted salicylic acids which have a relatively high softening point suitable for the division into fine pieces and dispersion have been in use as a developer. However, the developer having a high softening point has the following two disadvantages.

(1) Organic developers having a high softening point are so slow in rates of dissolution in a dye solution encapsulated in microcapsules, reaction with the dye and color development that it takes a long time before the density or color tone of a color image becomes constant after the microcapsules have been broken to permit the dye solution and the developer to contact. This tendency becomes more pronounced at lower temperatures, and a gentle variation of the color density with time has the relation with an instantaneous color developing characteristic. The variation of the color tone with time is considered as a problem especially for the development of black color from a plurality of mixed dyes.

(2) Developers having a high softening or melting point do not adhere to a substrate by softening or melting at a drying temperature of coating composition and thus require a slightly larger amount of an adhesive for fixing on the substrate. This tends to become more pronounced when using finer developers particles in order to improve the color density or instantaneous color developing properties, with the great possibility that one is disenabled to attain the purpose by the action of impeding the color development of the adhesive.

The softening point of the polyvalent metal salts of nuclear substituted salicylic acids is in close relation with the structure of the substituent. If a ring structure is contained as the substituent, the softening point is generally high. However, polyvalent metal salts of nuclear substituted salicylic acids having low softening and melting points are not always obtained solely based on the fact that any ring structure is not contained as a substituent. Polyvalents metal salts of nuclear substituted salicylic acids which are free of any ring structure as a substituent have been hitherto proposed including anacardic acid, 5-tertiary octylsalicylic acid, 3-methyl-5-tertiary octylsalicylic acid, 3,5-di-tertiary butylsalicylic acid, 3,5-di-tertiary amylsalicylic acid, 3-tertiary octyl-5-methylsalicylic acid or 3-tertiary octyl-5-ethylsalicylic acid. However, these are all compounds having a high melting point and are sparingly soluble in dye solution, so that a satisfactorily high color density cannot be attained.

SUMMARY OF THE INVENTION

An object of the invention is to provide a developer for pressure-sensitive recording sheets which ensures a high color density and a good instantaneous color developing characteristic and which is mainly composed of polyvalent metal salts of nuclear substituted salicylic acids having low softening and melting points.

Another object of the invention is to provide an aqueous dispersion of the developer mentioned above.

A further object of the invention is to provide a method for preparing the developer mentioned above.

According to the invention, there is provided a developer for pressure-sensitive recording sheets which comprises at least one polyvalent metal salt of a nuclear substituted salicylic acid of the following general formula [I]

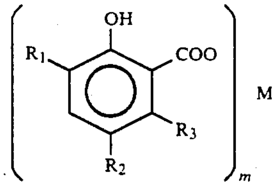

[I]

wherein $R_1$ represents an alkyl group having from 1 to 12 carbon atoms, $R_2$ represents a hydrogen atom or an alkyl group having from 1 to 12 carbon atoms, $R_3$ represents a hydrogen atom or a methyl group provided that at least one of $R_1$ and $R_2$ is a secondary butyl group, a secondary hexyl group, an isohexyl group, a secondary octyl group, an isononyl group, a secondary decyl group, a secondary dodecyl group or an isododecyl group and the total number of the carbon atoms in $R_1$, $R_2$ and $R_3$ is from 9 to 18, M is polyvalent metal atom, and m is a valence of M.

According to the invention, there is also provided a method for preparing a developer for pressure-sensitive recording sheets which comprises subjecting to double decomposition an aqueous solution of an alkali metal salt of a nuclear substituted salicylic acid of the following general formula [II]

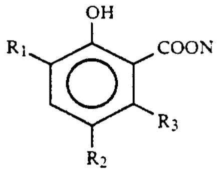

[II]

wherein $R_1$, $R_2$ and $R_3$ have, respectively, the same meanings as defined above, and N represents an alkali metal atom and an aqueous solution of a water-soluble polyvalent metal salt in the presence of an organic solvent whose solubility in water is not larger than 10 wt % and has a boiling point of from 60° C. to 180° C.

DETAILED DESCRIPTION OF THE INVENTION

Figure 1:
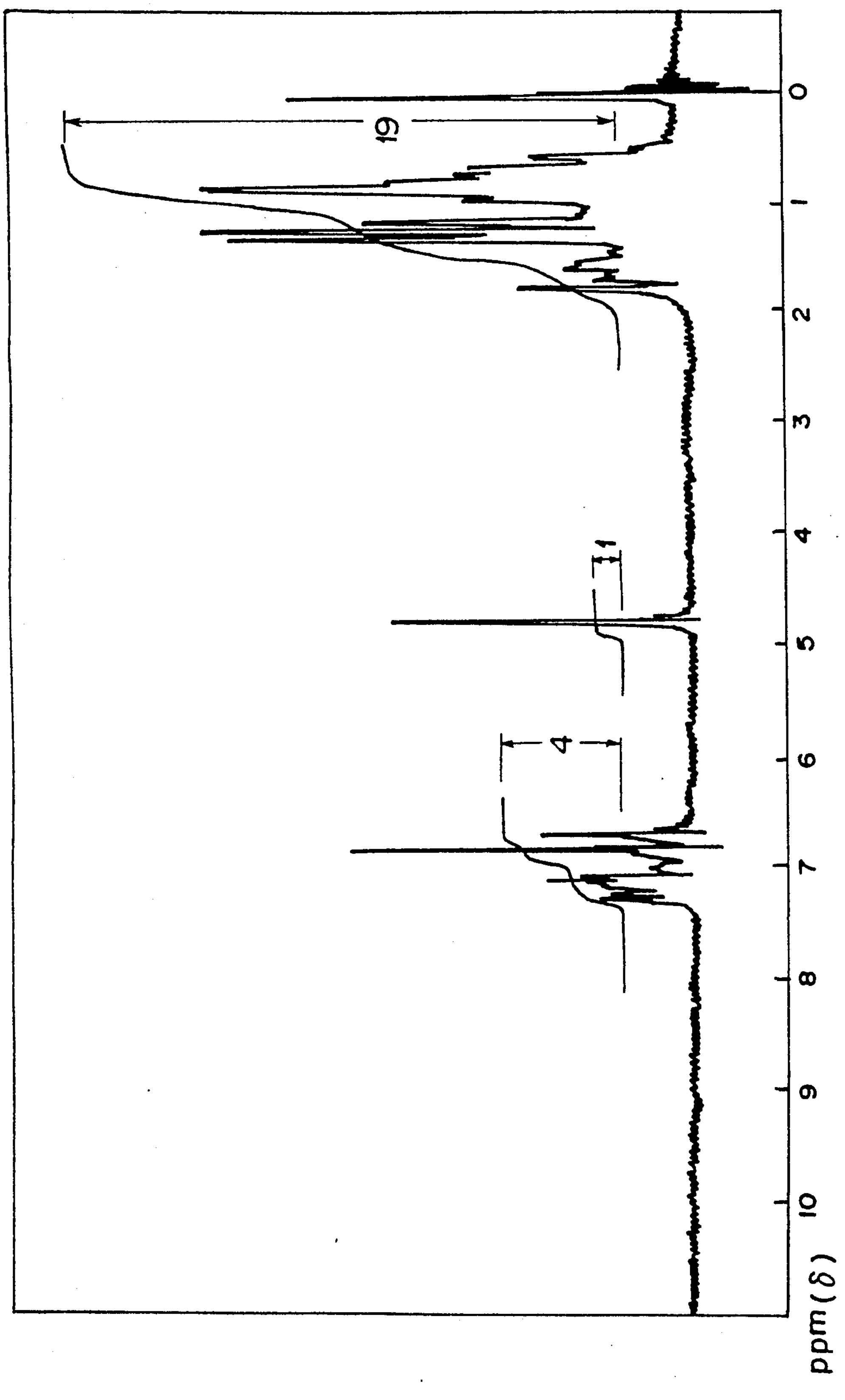
FIG. 1 is an NMR spectrum chart of 2-isononylphenol.

Developers having a low melting point and a low softening point generally exhibit a large solubility rate with respect to a dye solution with a rapid color developing reaction and a good instantaneous color developing characteristic and has a small variation in color tone with time. Moreover, when the developer has such a low softening point that it is able to be softened and fusingly deposited on a substrate at a drying temperature for the coating composition, the amount of an adhesive in a coating composition can be reduced because of the self adhesion of the developer. Thus, the color development impeding action of the adhesive can be suppressed to a minimum.

As described before, the softening point of the polyvalent metal salts of nuclear substituted salicylic acids is in close relation with the structures of the substituents. In order to obtain the salts having a sufficiently low melting point while reducing the crystallinity, choice of specific types of substituents is necessary. Polyvalent metal salts of salicylic acid which is nuclearly substituted with at least one group selected from a secondary butyl group, a secondary hexyl group, an isohexyl group, a secondary octyl group, an isononyl group, a secondary decyl group, a secondary dodecyl group and an isododecyl group are low in softening point and melting point. Preferably, the at least one group is a secondary octyl group, an isononyl group, a secondary decyl group, a secondary dodecyl group or an isododecyl group. It will be noted that the secondary hexyl group, secondary octyl group, secondary decyl group and secondary dodecyl group are intended to mean groups formed by addition of hexene, octene, decene and dodecene to salicylic acid, respectively. Likewise, the isohexyl group, isononyl group and isododecyl group mean those groups formed by addition of propylene dimer, propylene trimer and propylene tetramer or 1-butene trimer to salicylic acid, respectively. These groups are each not constituted of a single group but mixed groups based, for example, on optical or geometric isomerism. Accordingly, polyvalent metal salts of substituted salicylic acids having these groups are mixtures of a number of isomers. The reason why the compounds having these substituents are low in melting point is assumed as a result of the synergistic effect of these isomers on the depression of melting point. In fact, when two or more polyvalent metal salts of nuclear substituted salicylic acids obtained according to the invention are mixed, the melting point of the mixture always lowers.

In the general formula [I], $R_1$ represents an alkyl group having from 1 to 12 carbon atoms. If $R_1$ is a hydrogen atom, the color density becomes smaller and the resulting image is poorer in water resistance than in the case using the alkyl group. Presumably, this is because the alkyl group has a shielding effect on the hydroxyl group. Preferably, $R_1$ is an alkyl group having from 3 to 12 carbon atoms. This is based on the following test results.

(1) Zinc 3-isononylsalicylate>>zinc 5-isononylsalicylate.

(2) Zinc 3-isononyl-5-methylsalicylate>zinc 3-methyl-5-isononylsalicylate.

(3) Zinc 3-isononyl-5-isopropyl salicylate=zinc 3-isopropyl-5-isononyl salicylate.

This is a comparison where the color developability of the respective zinc salts are compared with respect to crystal violet lactone. The mark ">>" means a great difference in the color developability, the mark ">" means a slight difference in the color developability, and the mark "=" means no difference.

Specific examples of $R_1$ include a methyl group, an isopropyl group, a secondary butyl group, a tertiary butyl group, a tertiary amyl group, a secondary hexyl group, a isohexyl group, a secondary octyl group, an isononyl group, a secondary decyl group, a secondary dodecyl group, and a isododecyl group. Preferable examples for $R_1$ include an isopropyl group, a secondary butyl group, a tertiary butyl group, a tertiary amyl group, a secondary hexyl group, an isohexyl group, a secondary octyl group, an isononyl group, a secondary decyl group, a secondary dodecyl group, and an isododecyl group.

$R_2$ in the general formula [I] is a hydrogen atom or an alkyl group having from 1 to 12 carbon atoms and gives a less influence directly on the color developability than $R_1$. However, when $R_2$ is a hydrogen atom, there is a tendency that a developer undergoes a slight degree of browning when placed in a concentrated nitrogen oxide atmosphere. If this tendency is considered as unfavorable, $R_2$ should preferably be an alkyl group having from 1 to 12 carbon atoms. Specific examples include a methyl group, an ethyl group, an isopropyl group, a secondary butyl group, a tertiary butyl group, a tertiary amyl group, a secondary hexyl group, an isohexyl group, a secondary octyl group, an isononyl group, a secondary decyl group, a secondary dodecyl group and an isododecyl group.

The total of the carbon atoms in $R_1$. $R_2$ and $R_3$ greatly influences the hydrophilic and oleophilic properties of polyvalent metal salts of nuclear substituted salicylic acids. If the developer is hydrophilic in nature, the resultant color image does not satisfactorily become stable against water and moisture. Such a developer is generally poor in oleophilic property and does not sufficiently dissolve in a dye solution. If the total of the carbon atoms in $R_1$ and $R_2$ is small, the hydrophilic property is predominant. The total of the carbon atoms increases with an increasing tendency toward the oleophilic property. From this, those compounds where the total of the carbon atoms in $R_1$, $R_2$ and $R_3$ is not larger than 8 are outside the scope of the invention. On the other hand, when the total of the carbon atoms in $R_1$, $R_2$ and $R_3$ increases, the molecular weight of the nuclear substituted salicylic acid increases. The color developability decreases with an increase in size of the substituent, so that in order to ensure the same level of the color developability, a larger amount of developer is necessary. This is a reason why the total of the carbon atoms in $R_1$, $R_2$ and $R_3$ is limited to 18 or below, and is not thus always essential from the critical standpoint. In other words, developers exceeding the above limitation are not necessarily usable in the practice of the invention as having a serious defect. In general, however, the total of the carbon atoms in $R_1$, $R_2$ and $R_3$ is in the range of from 9 to 18, preferably from 10 to 13.

Examples of preferable nuclear substituted salicylic acids suitable for the purpose of the invention include 3-methyl-5-isononysalicylic acid, 3-methyl-5-isododecylsalicylic acid, 3-isopropyl-5-isononylsalicylic acid, 3-secondary butyl-5-isohexylsalicylic acid, 3-secondary butyl-5-isononylsalicylic acid, 3-tertiary butyl-5-isohexylsalicylic acid, 3-tertiary butyl-5-isononylsalicylic acid, 3-tertiary amyl-5-isohexylsalicylic acid, 3-tertiary amyl-5-isononylsalicylic acid, 3-secondary hexyl-5-secondary butylsalicylic acid, 3-secondary butyl-5-tertiary butylsalicylic acid, 3,5-disecondary hexylsalicylic acid, 3-secondary hexyl-5-isohexylsalicylic acid, 3-isohexyl-5-tertiary butyl salicylic acid, 3-isohexyl-5-secondary hexylsalicylic acid, 3,5-diisohexylsalicylic acid, 3-secondary octyl-5-methylsalicylic acid, 3-secondary octyl-6-methylsalicylic acid, 3-isononylsalicylic acid, 3-isononyl-5-methylsalicylic acid, 3-isononyl-5-ethylsalicylic acid, 3-isononyl-5-tertiary butylsalicylic acid, 3,5-diisononylsalicylic acid, 3-secondary decylsalicylic acid, 3-secondary decyl-5-methylsalicylic acid, 3-secondary decyl-6-methylsalicylic acid, 3-secondary dodecylsalicylic acid, 3-isododecylsalicylic acid, 3-isododecyl-5-methylsalicylic acid, 3-isododecyl-5-ethylsalicylic acid, 3-isododecyl-5-isopropylsalicylic acid and the like. More preferably, 3-isopropyl-5-isononylsalicylic acid, 3-tertiary butyl-5-isononylsalicylic acid, 3-isononyl-5-methylsalicylic acid, 3-isononyl-5-tertiary butylsalicylic acid, 3-secondary decylsalicylic acid, 3-secondary dodecylsalicylic acid, 3-isododecylsalicylic acid and 3-isododecyl-5-methylsalicylic acid are mentioned.

Polyvalent metals preferably used to form polyvalent metal salts with nuclear substituted salicylic acids for use as a developer include magnesium, aluminium, calcium, cobalt, nickel, strontium, tin and zinc, of which zinc is most preferred.

Most nuclear substituted salicylic acids used in the practice of the invention are novel compounds and can be prepared from industrially readily available starting materials by several known techniques. Main starting materials include, for example, phenol, salicylic acid, para-cresylic acid, meta-cresol, ortho-cresol, para-ethylphenol, para-isopropylphenol, para-secondary butylphenol, para-tertiary butylphenol, para-tertiary amylphenol, propylene, propylene dimer, propylene trimer, propylene tetramer, 1-butene, 1-butene trimer, isobutylene, isoamylene (isopentene), 1-hexene, octene, decene, dodecene, alkali hydroxides, carbon dioxide and the like.

The polyvalent metal salts of the nuclear substituted salicylic acids are obtained as water-insoluble salts by double decomposition reaction between aqueous solutions of alkali metal salts of corresponding nuclear substituted salicylic acids and aqueous solutions of water-soluble polyvalent metal salts. The resultant salts are, in most cases, resinous substances which are low in softening point and are very viscous in the vicinity of room temperature, thus being very difficult to handle as they are. When placed in water and heated, they are ready to flow and can thus be readily handled. Alternatively, addition of organic solvents results in a lowering of the viscosity, permitting easy handling. Preferably, when an organic solvent is used for the double decomposition reaction, the polyvalent metal salt of a nuclear substituted salicylic acid formed by the reaction immediately dissolves in the organic solvent with a lowering of the viscosity, so that the reaction proceeds smoothly even at low temperatures.

An intended compound obtained after the double decomposition has to be separated from an aqueous phase in the form of an oil phase. For this purpose, the organic solvent used should preferably have a small solubility in water, e.g. organic solvents having a solubility in water of not larger than 10 wt % are ordinarily used. The organic solvent used has to be removed, so that those solvents having a high boiling point are not favorable. In this sense, organic solvents having a boiling point of from 60° C. to 180° C. are used. Preferable examples of the organic solvent include benzene, toluene, xylene, ethylbenzene, chloroform, carbon tetrachloride, ethylene chloride, vinylidene chloride, 1,2-dichloroethylene, butanol, amyl alcohol, isopropyl ether, butyl ether, methyl ethyl ketone, methyl propyl ketone, methyl isobutyl ketone, ethyl acetate and the like. The amount of the solvent is in the range of from 0.05 to 5 parts by weight per unit part by weight of the polyvalent metal salt of nuclear substituted salicylic acid.

The polyvalent metal salts of nuclear substituted salicylic acids according to the invention are more or less hydrated in water with a lowering of the softening point by 50° C. to 80° C. Accordingly, milling or dispersion in water as will be ordinarily performed for organic developers is not appropriate. Where this inappropriate method has to be performed, the following measures should be taken: (1) milling or dispersion is effected at very low temperatures; (2) a resinous material having a high softening point is mixed; and (3) a milling aid such as an inorganic material having a great surface area is added.

For the fine dispersion of the polyvalent metal salt of nuclear substituted salicylic acid, it is preferably liquefied in water containing a dispersant by application of heat or by addition of an organic solvent and dispersed by emulsification The organic solvent used may be the same solvent as used for the double decomposition reaction. If the double decomposition product contains an organic solvent, the dispersion procedure may be effected without addition of any fresh solvent. The organic solvent may be azeotropically removed along with water after emulsification and dispersion, if required. The emulsification and dispersion media used for this purpose may be a supersonic homogenizer, a high pressure homogenizer, a homomixer, a sand grinder or the like. The dispersants used may be sodium alkylsulfates, sodium alkylsulfonates, sodium alkylarylsufonates, sodium salts of sulfosuccinic esters, sodium polyarylsulfonates, sodium polyacrylates, sodium polymethacrylates, sodium salts of maleic acid copolymers, polyvinyl alcohol, polyacrylamides, acrylamide copolymers, hydroxyethyl cellulose and the like.

In order to increase a practical value as a developer, the polyvalent metal salts of nuclear substituted salicylic acids may be mixed, prior to or after the dispersion, metal oxides, metal hydroxides, metal carbonates, polymer compounds, plasticizers, antioxidants, UV absorbers, other developers and the like.

When the polyvalent metal salts of nuclear substituted salicylic acids are applied as a developer on a pressure-sensitive recording sheet, they are usually dissolved in an organic solvent or dispersed in water to obtain a coating composition, followed by application and deposition onto a substrate. The coating composition may further comprise, depending upon purposes, inorganic pigments, clay minerals, dispersants, adhesives, thickening agents, antifoamers, antioxidants, UV absorbers, plasticizers, lubricants, organic solvents and the like.

The present invention is more particularly described by way of examples.

EXAMPLE 1

2,632 g (28 moles) of phenol and 15 g of fine granules of aluminium are charged into a hard glass five-necked flask equipped with an agitator, a thermometer, a reflux condenser, a dropping funnel and a nitrogen gas-introducing port and having an inner capacity of 5,000 ml. While gently blowing a nitrogen gas, the flask is heated and th content starts to be agitated when the temperature reaches 50° C. When the temperature is further raised until the content reaches 150° C., the aluminium dissolves while generating a hydrogen gas. After completion of the dissolution of the aluminium, the application of heat is so controlled that a liquid is refluxed portion by portion from the reflux condenser. Thereafter, 882 g (7.0 moles) of isononene (propylene trimer) is dropped from the dropping funnel over 10 hours. After completion of the dropping, the reaction is continued for 40 hours whereupon most isononene disappears. Then, the flask is cooled down to a temperature of the content of 90° C. Subsequently, 700 ml of 3N hydrochloric acid and 500 g of toluene are added, followed by violent agitation for 30 minutes while heating the flask. The content is transferred to a dropping funnel having an inner capacity of 5,000 ml and allowed to stand thereby separating into two phases. The lower aqueous phase is removed. 700 ml of hot water of 70° C. is further added and the dropping funnel is shaken and allowed to stand for phase separation. The above washing procedure is repeated twice. The oil phase is placed into a hard glass vacuum still having an inner capacity of 5,000 ml and subjected to removal of low boiling distillates until the still temperature reaches 150° C. under a vacuum of 25 Torr. The still residue is transferred to a hard glass vacuum still having an inner capacity of 2,000 ml and a fraction having a top temperature of from 105° C. to 110° C. under a vacuum of 1.2 Torr., are collected to obtain 1,280 g of a colorless transparent liquid. This liquid has a hydroxyl value of 253.2 (theoretical value: 254.6). According to the NMR analysis (FIG. 1), a peak pattern of the hydrogen in the benzene nucleus in the vicinity of 7 ppm is coincident with that of the phenol substituted at the 2 position and the ratios of absorption values of the hydrogen in the hydroxyl group near 5 ppm, the hydrogen in the benzene nucleus near 7 ppm and the hydrogen in the alkyl group near 1 ppm are 1:4:19. From this, the product is confirmed as 2-isononylphenol.

EXAMPLE 1-2

Figure 2:
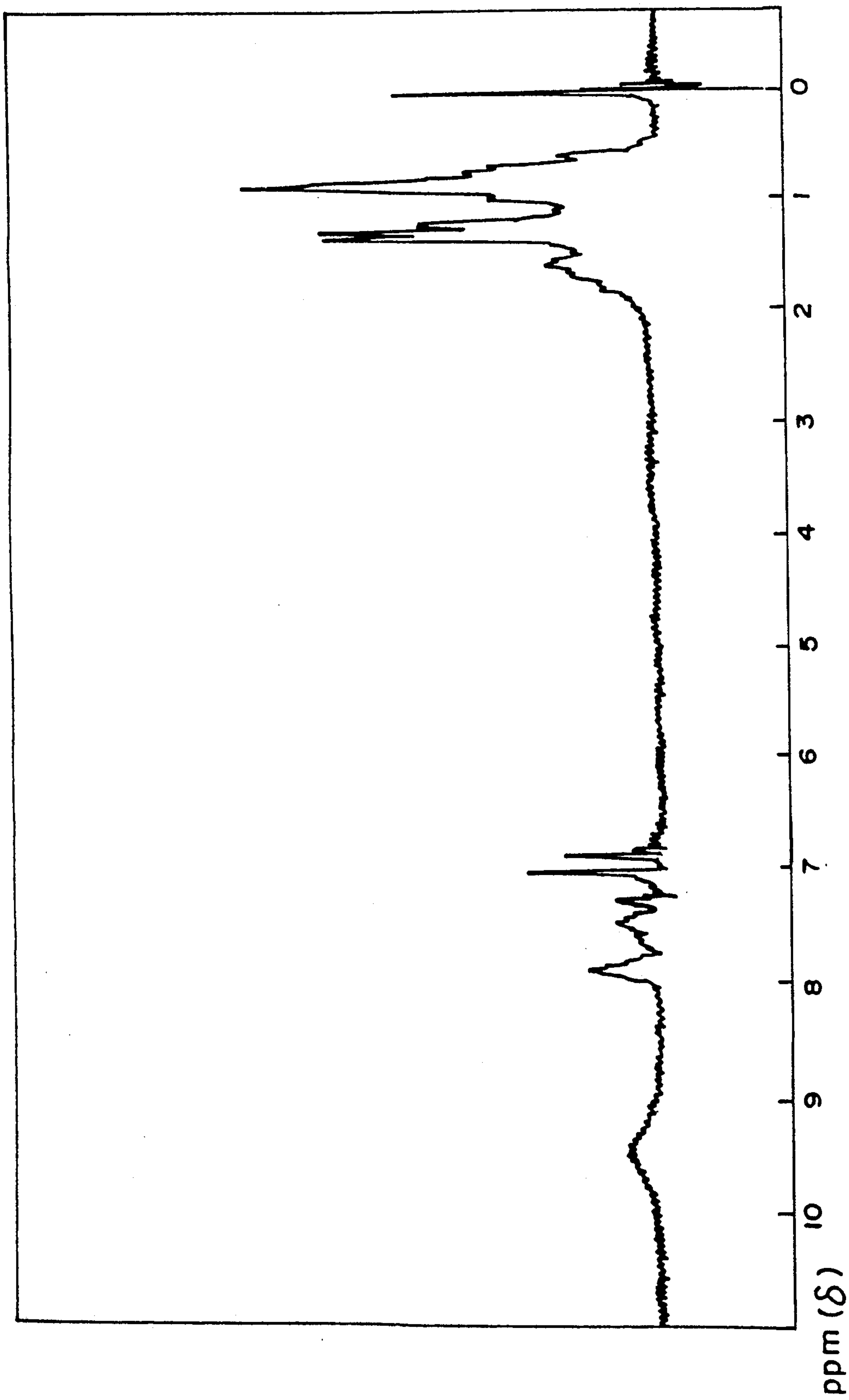
FIG. 2 is an NMR spectrum chart of 3-isononylsalicylic acid.
Figure 3:
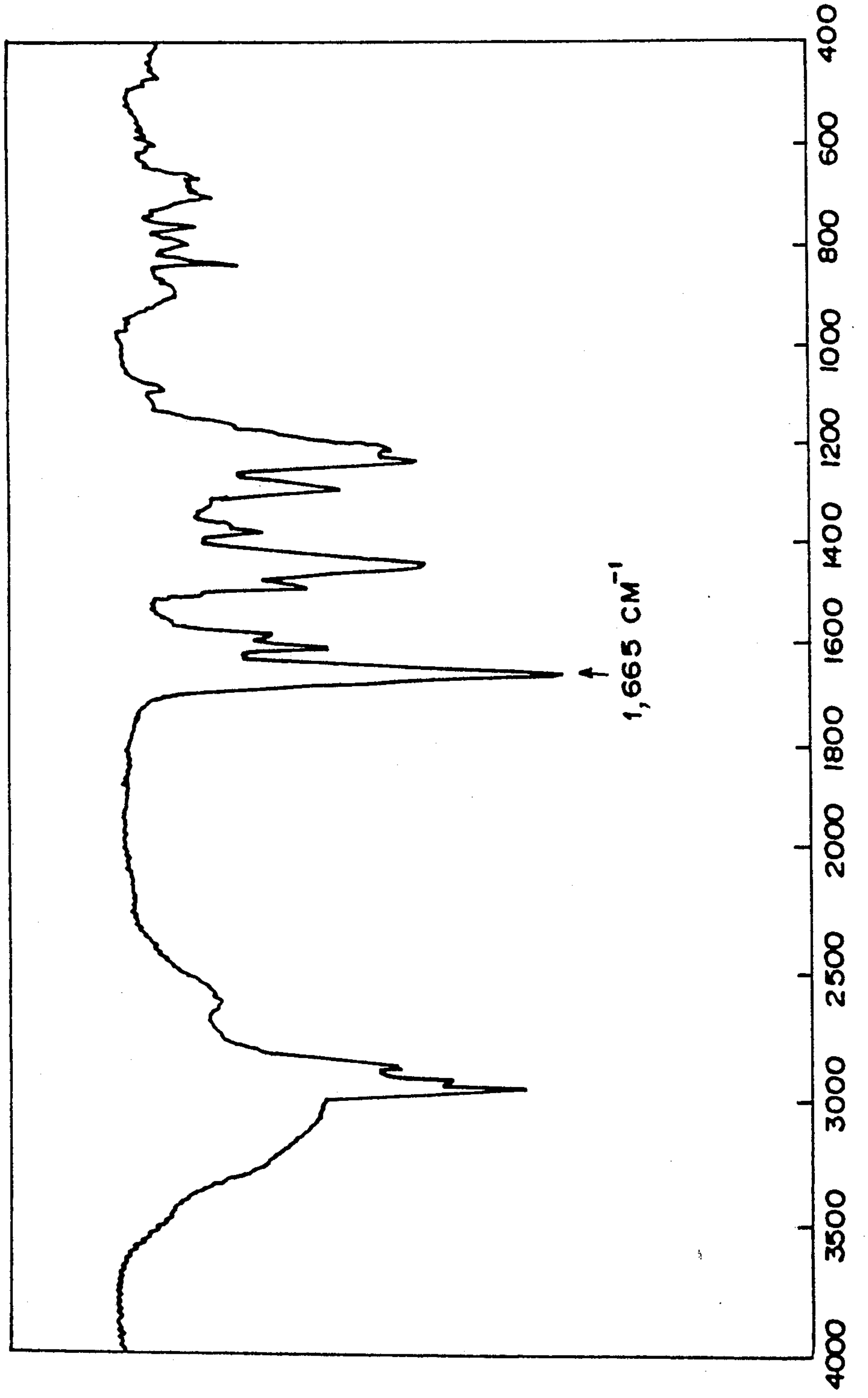
FIG. 3 is an IR absorption spectrum chart of of 3-isononylsalicylic acid.

440 g (2 moles) of the 2-isononylphenol obtained in Example 1, 250 g of toluene, 250 g of diethylene glycol dimethyl ether and 157 g (1.96 moles) of 50% sodium hydroxide are charged into a hard glass three-necked flask eqipped with an agitator, a thermometer and a device capable of azeotropically separating and removing water and having an inner capacity of 1,000 ml. While agitating, the flask is heated to azeotropically remove the water. After confirmation of the complete removal of the water, all the content is transferred to a stainless steel autoclave having an inner capacity of 1,000. Carbon dioxide is blown into the autoclave under a pressure of 15 kg/cm$^2$, followed by reaction at 170° C. until absorption of the carbon dioxide is not observed. The reaction completes within about 1 hour. The temperature of the content is decreased to 60° C., after which the content is poured into 6,000 ml of water. The aqueous solution and 1,000 g of toluene are charged into a hard glass four-necked flask equipped with an agitator, a thermometer, a reflux condenser and a stand-by port and having an inner capacity of 10,000 ml and the flask is heated under agitation so that the content is slightly boiled. The heating and agitation is stopped and the flask is allowed to stand, followed by removal of an upper toluene phase from the stand-by port. Again, 500 g of toluene is added, followed by agitation for 10 minutes, allowing the flask to stand and removal of the toluene phase. This washing procedure is repeated five times. The reflux condenser is replaced by a distillation tube, after which the flask is heated to remove toluene solubilized azeotropically with water. A dropping funnel is inserted into the stand-by port, from which 600 g of 20% diluted sulfuric acid is dropped while violently agitating the content. After completion of the dropping, further violent agitation is continued for 20 minutes, after which the content is allowed to stand, thereby causing a light brown viscous liquid to separate. After removal of the resultant aqueous phase, 1,000 ml of water is added and the flask is heated while violently agitating so that the content is slightly boiled, followed by allowing to stand and removal of the resultant aqueous phase. This washing procedure is repeated three times. The light brown viscous liquid is transferred to a hard glass vacuum still with an inner capacity of 1,000 ml, followed by removal of volatile components until the temperature of the still reaches 120° C. at a vacuum of 1.2 Torr. 482 g of the resultant product obtained after dehydration is a light brown viscous transparent liquid. The liquid has an acid value of 211 (theoretical value: 212.2). The NMR analysis (FIG. 2) reveals that a peak pattern of the hydrogen in the benzene nucleus in the vicinity of 7 ppm is coincident with the salicylic acid substituted at the 3 position. The IR absorption spectrum (FIG. 3) reveals that there is an absorption of the carbonyl group having a strong hydrogen bond at 1,665 $cm^{-1}$. From the above, the product is found to be 3-isononylsalicylic acid.

EXAMPLE 1-3

2,000 g of water containing 60 g of sodium hydroxide is charged into a hard glass beaker having an inner capacity of 3,000 ml, to which the 3-isononylsalicylic acid obtained in Example 1-2 is gradually added while agitating the content.

398 g of the 3-nonylsalicylic acid is required before the pH reaches 7. It is apparent that the resultant solution is an aqueous solution of sodium 3-isononylsalicylic acid. The analysis by liquid chromatography demonstrates a completely single peak. 1,800 g of an aqueous solution containing 200 g of zinc sulfate is charged into a hard glass four-necked flask equipped with an agitator, a thermometer, a reflux condenser and a dropping funnel and having an inner capacity of 5,000 ml, and the flask is heated under agitation to such an extent that the content is slightly boiled. While keeping this state, all the aqueous solution of the sodium salt is dropped into the solution. After completion of the dropping, the heating of the flask is immediately stopped, followed by further agitation for 30 minutes. When the flask is allowed to stand, a light brown viscous resinous substance is allowed to separate. After removal of the resultant aqueous phase, 1,000 ml of water is added, after which while heating the flask, the content is agitated and allowed to stand when boiled, followed by removal of the aqueous phase. This washing procedure is repeated twice. The resultant resinous substance contains about 8% of water. Part of the substance is taken out and dried in a vacuum dryer at a vacuum of 5 Torr., at 100° C. for 1 hour to give a sample for analysis. The product is a light brown transparent resinous substance having a content of zinc of 10.8% (the theoretical: 11.04%) and a softening point of 97° C., and is apparently confirmed to be zinc 3-isononylsalicylate.

EXAMPLE 1-4

300 g of toluene is added for dissolution to 400 g of the water-containing zinc 3-isononylsalicylate obtained in Example 1-3. The resultant solution is placed in a hard glass beaker having an inner capacity of 3,000 ml, to which 1,200 g of water containing 3 g of sodium dodecylbenzenesulfonic acid and 8 g of polyvinyl alcohol having a degree of saponification of 98% is added, followed by emulsification and dispersion in a homomixer (TK-M Type, made by Tokushu Kika Kogyo K.K.) at a frequency of 10,000 r.p.m. The resultant emulsion is placed in a hard glass three-necked flask equipped with an agitator, a thermometer and a distillation tube and having an inner capacity of 3,000 ml, followed by heating the flask at the bottom thereof under gentle agitation thereby azeotropically distilling off the toluene along with water. The liquid from which the toluene has been distilled off is milky in color and the disperse phase has an average size of 0.6 micrometers. When the emulsion is dried at a vacuum of 20 Torr, at a temperature of 100° C. for 1 hour. the content of the residue after the volatilization is 34.5%. This is an aqueous dispersion of zinc 3-isononylsalicylate.

EXAMPLE 2

Figure 4:
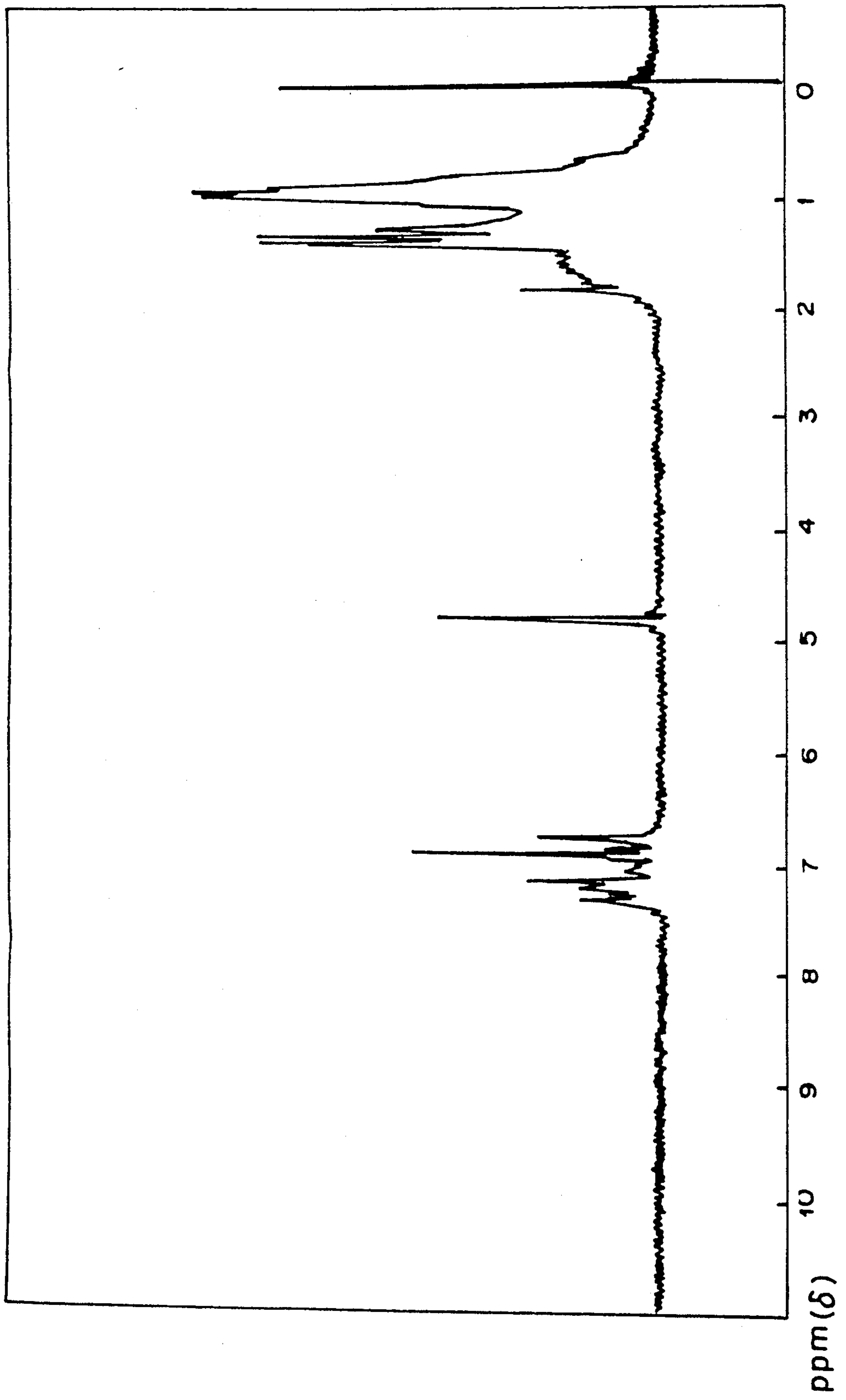
FIG. 4 is an NMR spectrum chart of 2-isododecylphenol.

2,632 g (28 moles) of phenol and 20 g of fine granules of aluminium are charged into a five-necked flask having an inner capacity of 5,000 ml. While blowing a nitrogen gas, the flask is heated to dissolve the aluminium in the same manner as in Example 1. While heating to such an extent that a liquid is refluxed portion by portion from the reflux condenser, 941 g (5.6 moles) of isododecene (propylene tetramer) is dropped from the dropping funnel over 15 hours. After completion of the dropping, the reaction is continued for 30 hours whereupon most isododecene disappears. Then, the flask is cooled down to a temperature of the content of 90° C. Subsequently, 800 ml of 3N hydrochloric acid and 400 g of toluene are added, followed by agitation for 1 hour while heating. The content is transferred to a dropping funnel having an inner capacity of 5,000 ml and the resultant aqueous phase is removed, followed by washing with water of 70° C. twice in the same manner as in Example 1. The oil phase is placed into a hard glass vacuum still or still having an inner capacity of 5,000 ml and subjected to removal of low boiling distillates until the still temperature reaches 150° C. under a vacuum of 20 Torr. The still residue is transferred to a hard glass vacuum still having an inner capacity of 2,000 ml and a fraction having a top temperature of from 130° C. to 138° C. under a vacuum of 1.2 Torr., are collected to obtain 1,120 g of a product. This product has a hydroxyl value of 215.0 (theoretical value: 213.8). According to the NMR analysis (FIG. 4), a peak pattern of the hydrogen in the benzene nucleus in the vicinity of 7 ppm is coincident with that of the phenol substituted at the 2 position as in Example 1, from which the product is confirmed as 2-isododecylphenol.

EXAMPLE 2-2

472 g (1.8 moles) of the 2-isododecylphenol obtained in Example 2, 300 g of xylene and 140 g (1.75 moles) of a 50% sodium hydroxide aqueous solution are charged into a three-necked flask having an inner capacity of 1,000 ml, followed by azeotropic removal of the water and xylene in the same manner as in example 1-2. The residue is transferred to an autoclave with an inner capacity of 1,000 ml, and reacted under a carbon dioxide pressure of 15 $kg/cm^2$ at 170° C. The reaction completes for approximately 1 hour.

Figure 5:
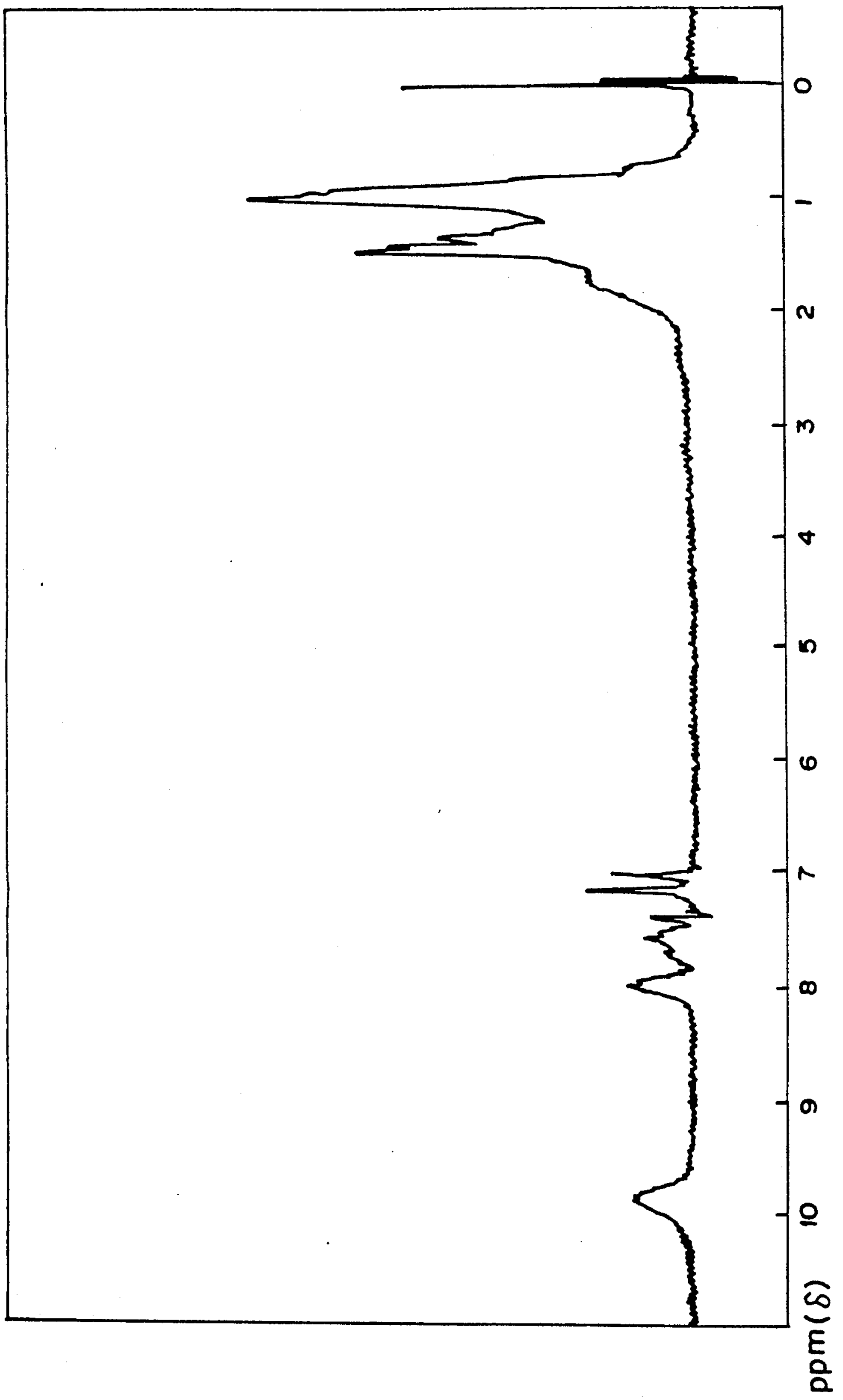
FIG. 5 is an NMR spectrum chart of 3-isododecylsalicylic acid.

6,000 ml of water, 500 g of xylene and 300 g of butanol are charged into a four-necked flask with an inner capacity of 10,000 ml, into which the content of the autoclave cooled down to 60° C. is charged while agitating. The flask is heated until the content is boiled, and allowed to stand, followed by removal of the upper phase. Moreover, the residue is washed five times with a mixture of 400 g of toluene and 100 g of butanol. The reflux condenser is changed with a distillation tube and the solvent azeotropically dissolved with water is removed. 50 g of the residue is placed in an Erlenmeyer flask for use as a sample for analysis. While heating the Erlenmeyer flask, 5 g of 20% dilute sulfuric acid is added, which is subsequently violently agitated and then allowed to stand, whereupon a light brown liquid separates, followed by removing the resultant aqueous phase and washing three times with 50 ml of water of 70° C. The light brown viscous liquid is dried at a vacuum of 5 Torr., at 100° C. for 1 hour to obtain a transparent liquid. The liquid has a single peak when subjected to liquid chromatography and has an acid value of 181.2 (the theoretical: 183.1). The NMR analysis (FIG. 5) reveals that the peak pattern completely coincides with that of the salicylic acid substituted at the 3 position in the same manner as in FIG. 2, from which the product is confirmed to be 3-isododecylsalicylic acid.

EXAMPLE 2-3

16 g of a 50% sodium hydroxide aqueous solution is added to the sodium 3-isododecylsalicylate obtained in Example 2-2. While heating to 90° C., 1,200 g of an aqueous solution containing 200 g of zinc sulfate is dropped into the solution. The mixture is further agitated for 30 minutes after the dropping and allowed to stand. The resultant aqueous phase is removed and 1,000 ml of hot water is added to the residue, followed by washing three times. About 10 g of the washed product is taken out and dried at a vacuum of 5 Torr., at 100° C. for 1 hour for use as a sample for analysis. The sample is a light brown transparent resinous substance which has a softening point of 93° C. and a content of zinc of 11.8% (the theoretical: 9.67%). The deviation in the zinc content from the theoretical is assumed to reside in the presence of zinc hydroxide and zinc carbonate.

EXAMPLE 2-4

200 g of xylene is added to the resinous substance obtained in example 2-3, to which is added 1,200 ml of water containing 3 g of sodium dibutylnaphthalenesulfonate and 6 g of polyvinyl alcohol having a degree of saponification of 98%, followed by emulsification and dispersion in a homomixer at 10,000 r.p.m., for 20 minutes. The resultant emulsion is placed in a flask having an inner capacity of 3,000 ml and subjected to removal of the xylene along with water by distillation. The residue has a dispersed phase having an average particle size of 0.4 micrometers with a content of non-volatile matters of 37.2% and is an aqueous dispersion of a developer mainly composed of zinc 3-isododecylsalicylate.

EXAMPLE 3

Figure 6:
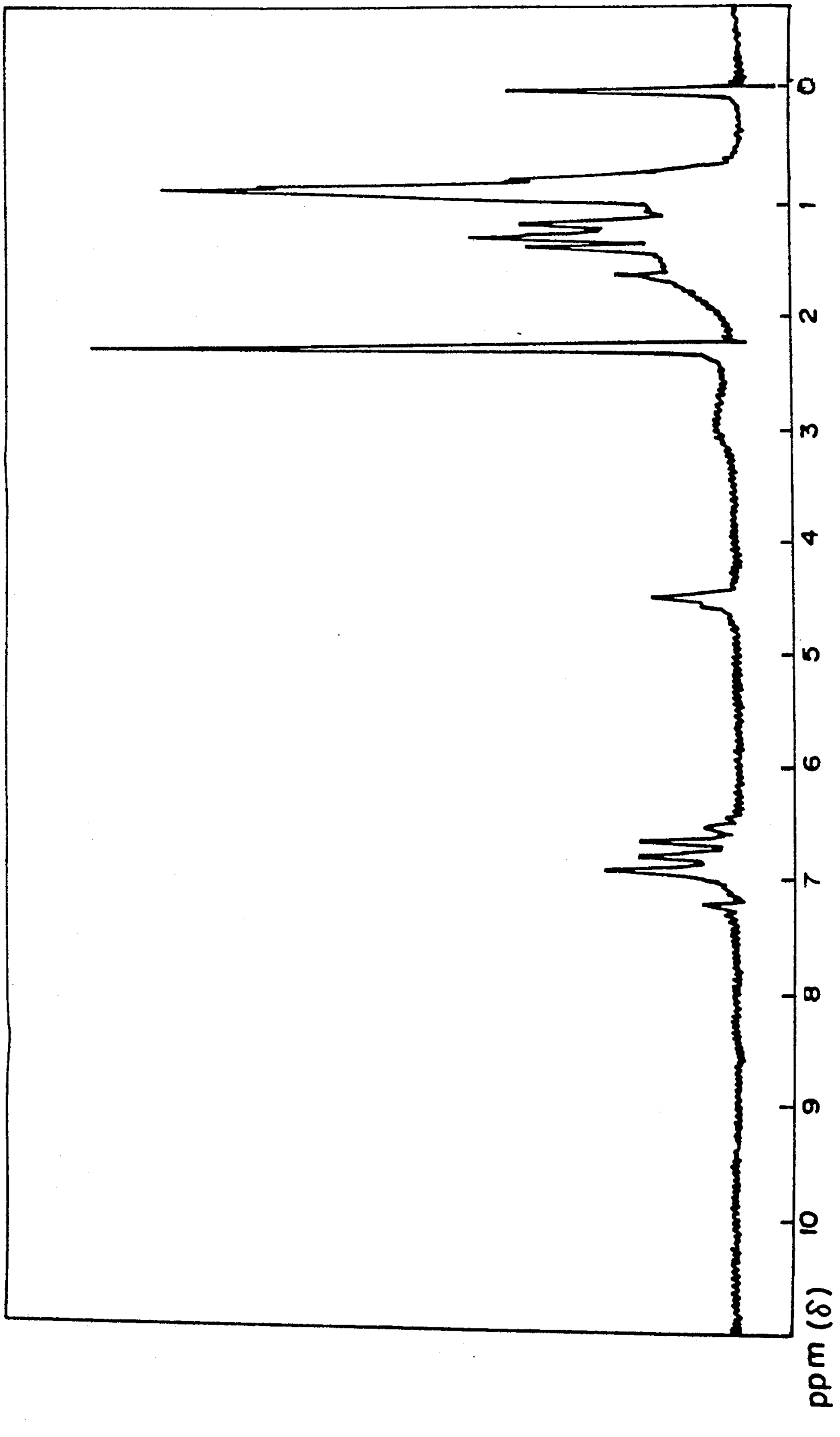
FIG. 6 is an NMR spectrum chart of 2-isononyl-4-methylphenol.

2,700 g (25 moles) of para-cresol and 14 g of fine granules of aluminium are charged into a four-necked flask having an inner capacity of 3,000 ml and the aluminium is dissolved substantially in the same manner as in Example 1. After completion of the dissolution of the aluminium, the solution is placed into an autoclave having an inner capacity of 5,000 ml. While keeping the content at a temperature of 230° C., 756 g (6 moles) of isononene is forced into the autoclave over 5 hours. Thereafter, the reaction is continued for 10 hours, after which the content is cooled down to a temperature of 90° C. The thus cooled content is placed into a four-necked flask with an inner capacity of 5,000 ml, followed by washing with diluted hydrochloric acid and hot water in the same manner as in Example 1. The washed product is subjected to vacuum distillation in the same manner as in Example 1 to collect 1,026 g of a fraction of a top temperature of from 105° C. to 110° C. at a vacuum of 1.0 Torr. The distillate product has a hydroxyl value of 238.8 (the theoretical: 239.4). According to the NMR analysis (FIG. 6), the peak pattern of the hydrogen in the benzene nucleus in the vicinity of 7 ppm coincides with phenols substituted with the 2,4 positions, from which the product is confirmed to be 2-isononyl-4-methylphenol.

EXAMPLE 3-2

An aqueous dispersion of zinc 3-isononyl-5-methylsalicylate is obtained in the same manner as in Examples 1-2 to 1-4.

EXAMPLE 4

2,700 g (25 moles) of para-cresol and 80 g of methanesulfonic acid are charged into a five-necked flask with an inner capacity of 5,000 ml. While keeping the content at a temperature of 180° C., 756 g of isononene is dropped thereinto over 5 hours. After completion of the dropping, the reaction is continued for 10 hours and the content is cooled down to a temperature of 90° C., followed by washing four times with 1,000 ml of hot water. The resultant product is subjected to vacuum distillation in the same manner as in Example 1 to collect 1,058 g of a fraction obtained at a top temperature of 113° C. to 118° C. at a vacuum of 1.2 Torr. This product has a hydroxyl value of 237.2 (the theoretical: 239.4). The NMR spectrum is the same as that of FIG. 6, form which it is confirmed as 2-isononyl-4-methylphenol. Subsequently, an aqueous dispersion of zinc 3-isononyl-5-methylsalicylate is obtained according to the procedures of Examples 1-2 to 1-4.

EXAMPLE 5

An aqueous dispersion of zinc 3-isononyl-5-ethylsalicylate is obtained in the same manner as in Examples 3 and 3-2 except that para-ethylphenol is used instead of para-cresol used in Example 3. The boiling point of 2-isononyl-4-ethylphenol which is an intermediate ranges from 109° C. to 114° C. at 1.1 Torr., and the hydroxyl value is 223.1 (the theoretical: 225.9).

EXAMPLE 6

In the same manner as in Example 3 using para-isopropylphenol instead of para-cresol, there is obtained 2-isononyl-5-isopropylphenol. This has a boiling point of from 132° C. to 140° C. at 1.2 Torr., and the hydroxyl value is 211.9 (the theoretical: 213.8). Subsequently, the procedures of Examples 2-2 to 2-4 are repeated to obtain an aqueous dispersion of zinc 3-isononyl-5-isopropylsalicylate.

EXAMPLE 7

The general procedure of example 6 is repeated except that para-tertiary butylphenol is used instead of the para-isopropylphenol of Example 6, thereby obtaining an aqueous dispersion of zinc 3-isononyl-5-tertiary butylsalicylate.

EXAMPLE 8

2-Isododecyl-4-methylphenol is obtained in the same manner as in example 3 using isododecene (propylene tetramer) instead of the isononene of Example 3. Subsequently, the general procedures of Examples 2-2 to 2-4 are repeated to obtain an aqueous dispersion of zinc 3-isododecyl-5-methylsalicylate.

EXAMPLE 9

In the same manner as in Example 8 using para-ethylphenol instead of the para-cresol of Example 8, there is obtained an aqueous dispersion of zinc 3-isododecyl-5-ethylsalicylate.

EXAMPLE 10

1,410 g (15 moles) of phenol and 70 g of activated clay are charged into a five-necked flask having an inner capacity of 5,000 ml. While gently blowing a nitrogen gas, the flask is heated and the content starts to be agitated when the temperature reaches 50° C., after which the temperature of the content is raised to 160° C. A mixture of 1,008 g (12 moles) of 1-hexene and 1,008 g of isohexene (propylene dimer) is dropped from a dropping funnel over 20 hours. After completion of the dropping, the reaction is continued for 10 hours, after which the content is cooled down to 100° C. The content is filtered by suction to remove the activated clay and then transferred to vacuum distillation still where it is distilled at a vacuum of 1.2 Torr., to collect 1,680 g of a fraction of 128° C. to 142° C. This product has a hydroxyl value of 209.8 (the theoretical: 213.8). According to the gas chromatographic analysis, there appear two groups of peaks which are approximating each other and are each composed of complicated peaks. These are considered to consist of a 2,6-substituted group of 2,6-di-secondary hexylphenol, 2-secondary hexyl-6-isohexylphenol and 2,6-diisohexylphenol and a 2,4-substituted group of 2,4-di-secondary hexylphenol, 2-secondary hexyl-4-isohexylphenol, 2-isohexyl-4-secondary hexylphenol and 2,4-diisohexylphenol.

EXAMPLE 10-2

The mixture obtained in Example 10 is treated in the same manner as in Examples 2-2 to 2-4 to obtain an aqueous dispersion of a mixture of zinc 3,5-disecondary hexylsalicylate, zinc 3-secondary-hexyl-5-isohexylsalicylate, zinc 3-isohexyl-5-secondary hexylsalicylate and zinc 3,5-diisohexylsalicylate.

EXAMPLE 11

27 g of aluminium is dissolved in 3,000 g of para-tertiary butylphenol and is transferred to an autoclave with an inner capacity of 5,000 ml. A mixture of 210 g (2.5 moles) of 1-hexene and 210 g (2.5 moles) of isohexene is forced at 230° C. Subsequently, the general procedure of Example 3 is repeated to obtain 938 g of an equimolar mixture of 2-secondary hexyl-4-tertiary butylphenol and 2-isohexyl-4-tertiary butylphenol. This has a hydroxyl value of 238.1 g (the theoretical: 239.4) and a boiling point of 112° C. to 119° C. at 1.2 Torr.

EXAMPLE 11-2

In the same manner as in Examples 1-2 to 1-4, there is obtained from the product of Example 11 an aqueous dispersion of a mixture of zinc 3-secondary hexyl-5-tertiary butylsalicylate and zinc 3-isohexyl-5-tertiary butylsalicylate.

EXAMPLE 12

2,350 g (25 moles) of phenol and 150 g of activated clay are charged into a five-necked flask having an inner capacity of 5,000 ml. While gently blowing a nitrogen gas, the content is heated until the temperature reaches 160° C. 1,512 g (12 moles) of isononene is dropped over 20 hours, followed by continuation for 10 hours. The reaction product is cooled down to 100° C. and filtration by suction to remove the activated clay. The residue is placed in a vacuum distillation still having the Raschig ring rectification column with a packing height of 750 mm and having an inner capacity of 5,000 ml where 1,910 g of a fraction of from 115° C. to 125° C. at a vacuum of 1.2 Torr., is collected. This distillate product has a hydroxyl value of 252.5 (the theoretical: 254.6). From the gas chromatographic analysis, it is confirmed to be a mixture of 2.8% of 2-isononylphenol and 97.2% of 4-isononylphenol.

EXAMPLE 12-2

7 g of aluminium is dissolved in 660 g of the product obtained in Example 12 and placed in an autoclave having an inner capacity of 1,000 ml. While keeping the temperature of the content at 240° C., 63 g of propylene is forced under pressure. When the inner pressure in the autoclave lowers, the content is treated in the same manner as in Example 1 to obtain 275 g of an intended product. This product has a hydroxyl value of 211.7 (the theoretical: 213.8) and a boiling point of from 128° C. to 138° C. at 1.2 Torr. According to the gas chromatography, the product is confirmed as a mixture of 0.3% of 4-isononylphenol, 0.9% of 2-isopropyl-6-isononylphenol, 96.8% of 2-isopropyl-4-isononylphenol and 2.0% of 2,6-diisopropyl-4-isononylphenol.

EXAMPLE 12-3

The product of Example 12-2 is treated in the same manner as in examples 2-2 to 2-4 to obtain an aqueous dispersion mainly composed of zinc 3-isopropyl-5-isononylsalicylate.

EXAMPLE 13

The product obtained in Example 12 is treated in the same manner as in Examples 12-2 and 12-3 except that 1-butene is used instead of the propylene of Example 12-2, thereby obtaining an aqueous dispersion mainly composed of zinc 3-secondary butyl-5-isononylsalicylate.

EXAMPLE 14

The product obtained in Example 12 is treated in the same manner as in Examples 12-2 and 12-3 except that isobutylene is used instead of the propylene of Example 12-2, thereby obtaining an aqueous dispersion mainly composed of zinc 3-tertiary butyl-5-isononylsalicylate.

EXAMPLE 15

The product obtained in Example 12 is treated in the same manner as in Examples 12-2 and 12-3 except that isopentene is used instead of the propylene of Example 12-2, thereby obtaining an aqueous dispersion mainly composed of zinc 3-tertiary amyl-5-isononylsalicylate.

EXAMPLE 16

The general procedure of Example 12 is repeated except that isohexene is used instead of the isononene of Example 12, thereby obtaining 4-isohexylphenol. This product has a hydroxyl value of 312.7 (the theoretical: 314.7) and a boiling point of from 93° C. to 97° C. at 1.2 Torr.

EXAMPLE 16-2

The product obtained in Example 16 is treated in the same manner as in Example 12-2 to obtain 2-isopropyl-4-isohexylphenol. This phenol has a hydroxyl value of 254.1 (the theoretical: 254.6) and a boiling point of from 103° C. to 108° C. at 1.2 Torr.

EXAMPLE 16-3

The product obtained in Example 16-2 is treated in the same manner as in Examples 1-2 to 1-4 to obtain an aqueous dispersion mainly composed of zinc 3-isopropyl-5-isohexylsalicylate.

EXAMPLE 17

The product obtained in Example 16 is treated in the same manner as in Example 13 to obtain an aqueous dispersion mainly composed of zinc 3-secondary butyl-5-isohexylsalicylate.

EXAMPLE 18

The product obtained in Example 16 is treated in the same manner as in Example 14 to obtain an aqueous dispersion of zinc 3-tertiary butyl-5-isohexylsalicylate.

EXAMPLE 19

The product obtained in Example 16 is treated in the same manner as in Example 15 to obtain an aqueous dispersion of zinc 3-tertiary amyl-5-isohexylsalicylate.

EXAMPLE 20

2,4-Disecondary butylphenol is obtained from para-secondary butylphenol and 1-butene in the same manner as in Example 3, followed by treatment in the same manner as in Examples 1-2 to 1-4 to obtain an aqueous dispersion mainly composed of zinc 3,5-disecondary butylsalicylate.

EXAMPLE 21

In the same manner as in Example 20 using 1-hexene instead of the 1-butene of Example 20, there is obtained an aqueous dispersion of zinc 3-secondary hexyl-5-secondary butylsalicylate.

EXAMPLE 22

2-Secondary hexyl-4-tertiary butylphenol is obtained from para-tertiary butylphenol and 1-hexene in the same manner as in Example 3, followed by treatment in the same manner as in Examples 1-2 to 1-4 to obtain an aqueous dispersion mainly composed of zinc 3-secondary hexyl-5-tertiary butylsalicylate.

EXAMPLE 23

In the same manner as in Example 22 using isohexene instead of the 1-hexene of Example 22, there is obtained an aqueous dispersion mainly composed of zinc 3-isohexyl-5-tertiary butylsalicylate.

EXAMPLE 24

2-Methyl-4-isononylphenol is obtained from ortho-cresol and isononene in the same manner as in Example 12, followed by treatment in the same manner as in Examples 1-2 to 1-4 to obtain an aqueous dispersion mainly composed of zinc 3-methyl-5-isononylsalicylate.

EXAMPLE 25

2-Methyl-4-isododecylphenol is obtained from ortho-cresol and isododecene in the same manner as in Example 12, followed by treatment in the same manner as in Examples 2-2 to 2-4 to obtain an aqueous dispersion mainly composed of zinc 3-methyl-5-isododecylsalicylate.

EXAMPLE 26

2-Isododecylphenol is obtained in the same manner as in Example 2 using 1-butene trimer instead of the isododecene (propylene tetramer) used in Example 2. This product is rarely distinguishable from the 2-isododecylphenol obtained in Example 2. Subsequently, the product is treated in the same manner as in Examples 2-2 to 2-4 to obtain an aqueous dispersion of zinc 3-isododecylsalicylate, which cannot be distinguished from the product obtained in Example 2-4.

EXAMPLE 27

An aqueous dispersion mainly composed of cobalt 3-isododecylsalicylate is obtained from the aqueous solution of sodium 3-isododecylsalicylate obtained in Example 2-2 and an aqueous solution of cobalt chloride in the same manner as in Examples 2-3 and 2-4.

EXAMPLE 28

An aqueous dispersion mainly composed of nickel 3-isododecylsalicylate is obtained from the aqueous solution of sodium 3-isododecylsalicylate obtained in Example 2-2 and an aqueous solution of nickel sulfate in the same manner as in Examples 2-3 and 2-4.

EXAMPLE 29

472 g (1.8 moles) of the 2-isododecylphenol obtained in Example 2, 300 g of xylene and a 50% sodium hydroxide aqueous solution were treated in the same manner as in Example 2-2 to obtain a sodium 3-isododecylsalicylate aqueous solution. 300 g of xylene is added to the solution, followed by dropping a 17% zinc sulfate aqueous solution while violently agitating. After completion of the dropping, agitation is continued for further 30 minutes and placed in a dropping funnel. The lower aqueous phase is removed from the funnel. The residue is washed three times with 1,000 ml of water and mixed with 1,200 ml of water containing 3 g of sodium dodecylbenzenesulfonate and 6 g of polyvinyl alcohol having a degree of saponification of 98%, followed by emulsification and dispersion in a homomixer at 10,000 r.p.m. for 20 minutes and removal of the xylene along with water by distillation, thereby obtaining an aqueous dispersion mainly composed of zinc 3-isododecylsalicylate having a content of non-volatile matters of 36.2%.

EXAMPLE 30

15 g of aluminium is dissolved in 2,720 g (20 moles) of para-isopropylphenol in a five-necked flask having an inner capacity of 5,000 ml, followed by reaction with 1,176 g (7 moles) of isododecene (propylene tetramer) in the same manner as in Example 2 to obtain 1,608 g of 2-isododecyl-4-isopropylphenol. This product has a hydroxyl value of 184.0 (the theoretical: 184.3) and a boiling point of 152° C. to 160° C. under a vacuum of 1.2 Torr.

EXAMPLE 30-2

456 g (1.5 moles) of the 2-isododecyl-4-isopropylphenol obtained in Example 30, 300 g of xylene and 120 g (1.5 moles) of a 50% sodium hydroxide aqueous solution were treated and dehydrated in the same manner as in Example 2-2. The residue is placed in an autoclave with an inner capacity of 1,000 ml, followed by reaction at a pressure of carbon dioxide of 20 kg/cm$^2$ at a temperature of 170° C. The content in the autoclave is cooled down to 80° C. and poured into 3,000 ml of water, followed by dropping 1,200 g of an aqueous solution of 15% zinc sulfate under violent agitation. After completion of the dropping, agitation is continued for 30 minutes and the content is placed in a dropping funnel. The resultant lower aqueous phase is removed and the residue is washed three times with 1,000 ml of water. The washed product is treated in the same manner as in Example 29 to obtain an aqueous dispersion mainly composed of zinc 3-isododecyl-5-isopropylsalicylate.

EXAMPLE 31

In the same manner as in Examples 30 and 30-2, there is obtained an aqueous dispersion of zinc 3,5-diisononylsalicylate from the 4-isononylphenol obtained in Example 12 and isononene.

EXAMPLE 32

100 parts of finely divided aluminosilicate, 10 parts of zinc oxide, 0.5 parts of polyvinyl alcohol having a degree of saponification of 98%, 10 parts, as a solid content, of each of the polyvalent metal salts of the nuclear substituted salicylates obtained in Examples 1 to 31 and zinc 3,5-dicyclohexylsalicylate (Reference 1) and zinc 3,5-di(α-methylbenzyl)salicylate (Reference 2), and water in an amount sufficient to make 300 parts in total are mixed and dispersed in a pot sand grinder with an inner capacity of 1,000 ml at a frequency of 2,000 r.p.m., for 10 minutes. 100 parts of an aqueous solution of polyvinyl alcohol having a degree of saponification of 98% and 10 parts (as solids) of a carboxy-modified styrene-butadiene latex are added to the resultant dispersion, to which water is added sufficiently to make a coating composition having a total solid content of 20%. This coating composition is coated by means of a bar coater on a paper sheet having a weight of 50 g per square meter in an amount of 6 $g/m^2$ on the dry basis, followed by drying to obtain a pressure-sensitive recording sheet.

The above procedure is repeated except that the amount of the respective polyvalent metal salts of the nuclear substituted salicylic acids is reduced to $\frac{1}{3}$ to obtain pressure-sensitive recording sheets for comparison.

An upper leaf of a commercially available pressure-sensitive recording sheet using Crystal Violet lactone as a dye and diisopropylnaphthalene as a solvent is superposed on the respective pressure-sensitive recording sheets for comparison, followed by printing with an electric typewriter and allowing to stand in a room at 20° C. for 24 hours to give a recording density for comparison. The pressure-sensitive recording sheets obtained above are each superposed with the commercial upper leaf and printed with an electric typewriter in a room cooled to −10° C. The time (seconds) is measured until the recording density is visually observed as equal to that of the respective sheets for comparison and is used as a measure for instantaneous color developability. Thereafter, the printed sheets are transferred to a room controlled at 20° C. where they are allowed to stand for 24 hours, after which color densities are visually observed and evaluated by five ranks. (5: most dense, 4: fairly dense, 3: slightly dense, 2: equal to that of an ordinary commercial product, 1: slightly poor). The results are shown in Table 1. In Table 1, there are also shown a softening point of the respective polyvalent metals salts of nuclear substituted salicylic acids obtained in the examples and an average particle size (micrometers) of a dispersed phase in the respective employed emulsified dispersions.

TABLE 1

| Example | Instantaneous Color Developability | Color Density | Softening Point | Average Particle Size |
|---|---|---|---|---|
| 1 | 16 | 4 | 97° C. | 0.6 |
| 2 | 10 | 5 | 93 | 0.4 |
| 3 | 15 | 4 | 96 | 0.5 |
| 4 | 13 | 5 | 94 | 0.6 |
| 5 | 12 | 5 | 94 | 0.5 |
| 6 | 9 | 5 | 92 | 0.4 |
| 7 | 12 | 4 | 100 | 0.4 |
| 8 | 8 | 5 | 90 | 0.4 |
| 9 | 9 | 4 | 91 | 0.4 |
| 10 | 11 | 4 | 98 | 0.8 |
| 11 | 21 | 4 | 112 | 0.7 |
| 12 | 8 | 5 | 91 | 0.5 |
| 13 | 8 | 5 | 90 | 0.4 |
| 14 | 14 | 5 | 102 | 0.6 |
| 15 | 13 | 4 | 98 | 0.6 |
| 16 | 23 | 3 | 108 | 0.9 |
| 17 | 24 | 3 | 114 | 0.8 |
| 18 | 28 | 3 | 116 | 0.7 |
| 19 | 22 | 3 | 113 | 0.7 |
| 20 | 31 | 3 | 118 | 1.0 |
| 21 | 26 | 3 | 109 | 0.9 |
| 22 | 25 | 3 | 117 | 1.0 |
| 23 | 21 | 3 | 119 | 1.0 |
| 24 | 19 | 3 | 101 | 0.9 |
| 25 | 12 | 4 | 95 | 0.8 |
| 26 | 9 | 5 | 94 | 0.4 |
| 27 | 9 | 3 | 91 | 0.6 |
| 28 | 7 | 3 | 95 | 0.7 |
| 29 | 11 | 5 | 96 | 0.5 |
| 30 | 6 | 4 | 62 | 0.4 |
| 31 | 5 | 3 | 53 | 0.4 |
| Reference 1 | 75 | 2 | over 150 | 1.2 |
| Reference 2 | 43 | 3 | 135 | 0.6 |

EXAMPLE 33

2,700 g of para-cresol and 20 g of trifluoromethanesulfonic acid are charged into a hard glass five-necked flask equipped with an agitator, a thermometer, a reflux condenser, a dropping funnel and a nitrogen gas-blowing port and having an inner capacity of 5,000 ml. While blowing a nitrogen gas gently, the flask is heated until the content reaches a temperature of 100° C. At the temperature, 1,400 g of 1-octene is dropped from the dropping funnel over 5 hours, followed by keeping the temperature at 100° C. for further 1 hour. 500 ml of water is added to the mixture and agitated sufficiently, followed by allowing it to stand and removal of the resultant aqueous phase. The above washing procedure is repeated three times. The resultant phase is subjected to vacuum distillation to collect a fraction of 105° C. to 118° C. at 1.5 Torr., in an amount of about 2,400 g. The analysis by a gas chromatograph using a capillary column reveals that the product is composed of three components including about 60% of 2-(octane-2-yl)-4-methylphenol, about 23% of 2-(octane-3-yl)-4-methylphenol and about 17% of 2-(octane-4-yl)-4-methylphenol. The product has a hydroxyl value of 253 (the theoretical: 254.6). From the above, the product is found to be 2-secondary octyl-4-methylphenol.

EXAMPLE 33-2

440 g (2 moles) of the 2-secondary octyl-4-methylphenol, 200 g of toluene, 200 g of diethylene glycol dimethyl ether and 157 g (1.96 moles) of a 50% sodium hydroxide aqueous solution are charged into a hard glass three-necked flask equipped with an agitator, a thermometer and a device capable of azeotropically separating and removing water and having an inner capacity of 1,000 ml. The flask is heated under agitation to azeotropically remove the water. After confirmation of complete removal of the water, all the content is transferred to a stainless steel autoclave having an inner capacity of 1,000 ml. Carbon dioxide is blown into the autoclave under a pressure of 15 kg/cm$^2$, followed by reaction at 170° C. until the carbon dioxide is not absorbed. After about one hour the reaction is completed. The temperature of the content is lowered to 60° C., after which it is poured into 6,000 ml of water. The aqueous solution and 1,000 ml of toluene are charged into a hard glass four-necked flask equipped with an agitator, a thermometer, a reflux condenser and a stand-by port and having an inner capacity of 10,000 ml. While agitating, the flask is heated so that the content is slightly boiled. The heating and agitation is stopped and the flask is allowed to stand, after which the upper toluene phase is removed from the stand-by port. Again, 500 g of toluene is added, followed by agitation for 10 minutes, allowing the flask to stand and removal of the toluene layer. The above washing procedure is repeated five times. The reflux condenser is replaced by a distillation tube and the flask is heated to remove the toluene azeotropically solubilized with water. A dropping funnel is set into the stand-by port, from which 600 g of 20% diluted sulfuric acid is dropped while violently agitating the content. After completion of the dropping, the content is violently stirred for 20 minutes and allowed to stand, thereby permitting a light brown viscous liquid to separate. After removal of the aqueous phase, 1,000 ml of water is added and the flask is heated under violent agitation so that the content is slightly boiled, followed by allowing to stand and removal of the resultant aqueous phase. The above washing procedure is repeated three times. The light brown viscous liquid is transferred to a hard glass vacuum distillation still having an inner capacity of 1,000 ml, followed by removal of volatile components until the still temperature reaches 120° C. at a vacuum of 1.2 Torr. 476 g of the resultant product obtained after dehydration is a light brown viscous transparent liquid with an acid value of 210 (the theoretical: 212.2). This product is confirmed to be 3-secondary octyl-5-methylsalicylic acid.

EXAMPLE 33-3

2,000 g of water containing 60 g of sodium hydroxide is charged into a hard glass beaker having an inner capacity of 3,000 ml. While agitating the content, the 3-secondary octyl-5-methylsalicylic acid obtained in Example 33-2 is gradually added. 398 g of the 3-secondary octyl-5-methylsalicylic acid is required until the pH reaches 7. This solution is apparently an aqueous solution of sodium 3-secondary octyl-5-methylsalicylate. The liquid chromatographic analysis reveals a completely single peak. 1,800 g of an aqueous solution containing 200 g of zinc sulfate is charged into a hard glass four-necked flask equipped with an agitator, a thermometer, a reflux condenser and a dropping funnel and having an inner capacity of 5,000 ml, and the flask is heated under agitation so that the content is slightly boiled. While keeping this state, all the sodium salt aqueous solution is dropped. After completion of the dropping, the heating of the flask is immediately stopped, followed by agitation for further 30 minutes. When the flask is allowed to stand, a light brown viscous liquid is permitted to separate. After removal of the resultant aqueous phase, 1,000 ml of water is added and agitated while heating the flask. When the content is boiled, it is allowed to stand and the resultant aqueous phase is removed. This washing procedure is repeated twice. The resultant resinous substance contains about 8% of water. Part of the substance is taken out and dried in a vacuum dryer at a vacuum of 5 Torr., at 100° C. for 1 hour to give a sample for analysis. This sample is a light brown transparent resinous substance having a zinc content of 10.8% (the theoretical: 11.04%) and a softening point of 97° C., and is apparently zinc 3-secondary octyl-4-methylsalicylate.

EXAMPLE 33-4

300 g of toluene is added to 400 g of the water-containing zinc 3-secondary octyl-5-methylsalicylate obtained in Example 33-3 for dissolution. The solution is placed in a hard glass beaker having an inner capacity of 3,000 ml, to which 1,200 g of water containing 3 g of sodium dodecylbenzenesulfonate and 8 g of polyvinyl alcohol having a degree of saponification of 98% is added, followed by emulsification and dispersion in a homomixer (TK-M, made by Tokushu Kika Kogyo K.K.) at 10,000 r.p.m., for 15 minutes. The resultant emulsion is transferred to a hard glass three-necked flask equipped with an agitator, a thermometer and a distillation tube and having an inner capacity of 3,000 ml. While gently agitating, the flask is heated at the bottom thereof to azeotropically remove the toluene along with water by distillation. The liquid from which the toluene has been distilled off is milky in color and the dispersed phase has an average particle size of 0.8 micrometers. When the liquid is dried at a vacuum of 20 Torr., at 100° C. for 1 hour, the content of the residue after volatilization is 36.8%. This is an aqueous dispersion of zinc 3-secondary octyl-5-methylsalicylate.

EXAMPLE 34

3,024 g (28 moles) of meta-cresol and 20 g of fine granules of aluminium are charged into a hard glass five-necked flask having an inner capacity of 5,000 ml. While blowing a nitrogen gas, the flask is heated to dissolve the aluminium. The content is cooled down to 150° C. and transferred to a stainless steel autoclave having an inner capacity of 10,000 ml where the content is heated. When the temperature of the content reaches 240° C., 2,016 g (18 moles) of 1-octene is charged into the autoclave in about 8 hours under pressure while keeping the temperature. After completion of the charging, the temperature is kept for 4 hours, after which the content is cooled. The thus cooled content is transferred to a hard glass dropping funnel having an inner capacity of 10,000 ml, to which 1,000 g of toluene and 800 ml of 3N hydrochloric acid are added for washing. Moreover, the content is washed twice with 800 ml of hot water. The oil phase is placed in a vacuum distillation still to collect a fraction with a top temperature of from 105° C. to 110° C. at a vacuum of 1.2 Torr., in an amount of about 3,200 g. According to the analysis by gas chromatography using a capillary column, the fraction is found to be made of 2-(octene-2-yl)-5-methylphenol and a small amount of other isomers. The hydroxyl value is 253.6 (the theoretical: 254.6). From the above, the product is found to be 2-secondary octyl-5-methylphenol.

EXAMPLE 34-2

In the same manner as in Example 33-2, 3-secondary octyl-6-methylsalicylic acid having an acid value of 209.5 (the theoretical: 212.22 is obtained from the 2-secondary octyl-5-methylphenol obtained in Example 34.

EXAMPLE 34-3

In the same manner as in Examples 33-3 and Example 33-4, an aqueous dispersion of zinc 3-secondary octyl-6-methylsalicylate having a content of a dried residue of 41.2% is obtained from the 3-secondary octyl-6-methylsalicylic acid obtained in Example 34-2.

EXAMPLE 35

1,880 g (20 moles) of phenol and 10 g of trifluoromethanesulfonic acid are charged into a five-necked flask equipped with an agitator, a thermometer, a gas-introducing port, a dropping funnel and a reflux condenser and having an inner capacity of 5,000 ml. While blowing a nitrogen gas from the introducing port, the content is agitated. The content is kept at a temperature of 50° C., into which 2,856 g (20×1.7 moles) of 1-hexene is dropped in about 5 hours from the dropping funnel. The temperature is kept for further 1 hour, after which the content is washed five times with 500 ml of water to remove the trifluoromethanesulfonic acid. The washed content is subjected to vacuum distillation to collect a fraction of from 145° C. to 180° C. at 1 Torr. The fraction has a hydroxyl value of 212 and is found to be a mixture of about 31% of 2,6-disecondary hexylphenol, about 67% of 2,4-disecondary hexylphenol and about 2% of 2,4,6-trisecondary hexyl phenol by gas chromatography.

EXAMPLE 35-2

In the same manner as in Example 33-2, 3,5-disecondary hexyl salicylic acid is obtained from the product obtained in Example 35. This acid has an acid value of 184. The sodium hydroxide used in this example is equimolar to the 2,4-disecondary hexylphenol in the composition.

EXAMPLE 35-3

In the same manner as in Example 33-3 and 33-4, an aqueous dispersion of zinc 3,5-disecondary hexylsalicylate having a content of a dried residue of 38.6% is obtained from the 3,5-disecondary hexylsalicylic acid obtained from Example 35-2.

EXAMPLE 36

In the same manner as in the foregoing examples, there are obtained:

(1) an aqueous dispersion of zinc 3-secondary-decylsalicylate having a content of a dried residue of 42.2% from phenol and 1-decene;

(2) an aqueous dispersion of zinc 3-secondary-decyl-5-methylsalicylate having a content of a dried residue of 35.8% from para-cresol and 1-decene;

(3) an aqueous dispersion of zinc 3-secondary decyl-6-methylsalicylate having a content of a dried residue of 38.5% from meta-cresol and 1-decene; and (4) an aqueous dispersion of zinc 3-secondary dodecylsalicylate having a content of a dried residue of 43.0% from phenol and 1-dodecene.

EXAMPLE 37

100 parts of finely divided aluminosilicate. 10 parts of zinc oxide. 0.5 parts of polyvinyl alcohol having a degree of saponification of 98%, 10 parts, as a solid, of each of the polyvalent metal salts of nuclear substituted salicylic acids obtained in Examples 33 to 36 and zinc 3,5-dicyclohexylsalicylate (Reference 3) and zinc 3,5-di(α-methylbenzyl)salicylate (Reference 4) and water in an amount sufficient to make 300 parts of a total composition. Each composition is dispersed by means of a pot sand grinder with an inner capacity of 1,000 ml at a frequency of 2,000 r.p.m., for 10 minutes. The resulting dispersion is mixed with 100 parts of an aqueous solution of polyvinyl alcohol having a degree of saponification of 98% and 10 parts (as a solid) of a carboxy-modified styrene-butadiene latex, to which water is added in an amount sufficient to make a total content of solids of 20%, thereby preparing a coating composition. The coating composition is applied onto a paper sheet with a weight of 50 g per square meter in an amount of 6 g per square meter on the dry basis and dried to obtain a pressure-sensitive secondary sheet. In the same manner as described above except that the polyvalent metal salts of the nuclear substituted salicylic acids are reduced to ⅓, thereby obtaining pressure-sensitive recording sheets for comparison. An upper leaf of a commercially available pressure-sensitive recording sheet using crystal violet lactone as a dye and diisopropylnaphthalene as a solvent is superposed on each of the pressure-sensitive recording sheets for comparison, followed by printing with an electric typewriter and allowing to stand in a room of 20° C. for 24 hours for comparative purposes for recording density. The pressure-sensitive recording sheets of the invention are each superposed with a commercial upper leaf and printed by the use of an electric typewriter in a room cooled to −10° C. Thereafter, the time (seconds) is measured until the recording density is equal to that of a corresponding sheet for comparison through visual observation and is used as a measure for instantaneous color developability. Subsequently, the typewritten sheets are transferred to a room of 20° C. After 24 hours, color densities are compared and evaluated by five ranks (5: most dense; 4: fairly dense; 3: slightly dense; 2: equal to that of an ordinary commercial sheet; 1: slightly poor). The results are shown in Table 2. In Table 2, the average size (micrometers), in emulsified dispersions, of the polyvalent metal salts of nuclear substituted salicylic acids obtained in the examples is also described.

TABLE 2

| Example | Instantaneous Color Developability | Color Density | Average Particle Size |
|---|---|---|---|
| 33-4 | 9 | 5 | 0.6 |
| 34-3 | 10 | 5 | 0.7 |
| 35-3 | 8 | 5 | 0.7 |
| 36-1 | 15 | 4 | 0.5 |
| 36-2 | 20 | 4 | 0.6 |
| 36-3 | 15 | 4 | 0.5 |
| 36-4 | 18 | 4 | 0.7 |
| Reference 3 | 75 | 2 | 1.2 |
| Reference 4 | 43 | 3 | 0.6 |

As will become apparent from the foregoing examples, the developer of the invention is low in melting and softening points and are significantly improved in instantaneous color developing characteristic and color density of color image.

What is claimed is:

1. A developer for pressure-sensitive recording sheets which comprises at least one polyvalent metal salt of a nuclear substituted salicylic acid selected from the group consisting of 3,5-disecondary hexylsalicylic acid, 3-5-diisohexylsalicylic acid, 3-secondary decylsalicylic acid, 3-secondary decyl-5-methylsalicylic acid, 3-secondary decyl-6-methylsalicylic acid, 3-secondary dodecylsalicylic acid, 3-isododecylsalicylic acid and 3-isododecyl-5-methylsalicylic acid.

2. An aqueous dispersion of a developer for pressure-sensitive recording sheets which comprises at least one polyvalent metal salt of a nuclear substituted salicylic acid selected from the group consisting of 3,5-disecondary hexylsalicylic acid, 3,5-diisohexylsalicylic acid, 3-secondary decylsalicylic acid, 3-secondary decyl-5-methylsalicylic acid, 3-secondary decyl-6-methylsalicylic acid, 3-secondary dodecylsalicylic acid, 3-isododecylsalicylic acid and 3-isododecyl-5-methylsalicylic acid.

3. A developer according to claim 1, wherein said nuclear substituted salicylic acid is a member selected from the group consisting of 3-secondary decyl-5-methylsalicylic acid, 3-secondary decyl-6-methylsalicylic acid, 3-secondary dodecylsalicylic acid, 3-isododecylsalicylic acid and 3-isododecyl-5-methylsalicylic acid.

4. A developer according to claim 1, wherein said polyvalent metal salt of the nuclear substituted salicylic acid is zinc salt of the nuclear substituted salicylic acid.

5. A method for preparing a developer for pressure-sensitive recording sheets which comprises at least one polyvalent metal salt of a nuclear substituted salicylic acid, the method comprising subjecting to double decomposition an aqueous solution of an alkali metal salt of a nuclear substituted salicylic acid selected from the group consisting of 3,5-disecondary hexylsalicylic acid, 3,5-diisohexyl-salicylic acid, 3-secondary decylsalicylic acid, 3-secondary decyl-5-methylsalicylic acid, 3-secondary decyl-6-methylsalicylic acid, 3-secondary dodecylsalicylic acid, 3-isododecylsalicylic acid and 3-isododecyl-5-methylsalicylic acid, and an aqueous solution of a water-soluble polyvalent metal salt in the presence of an organic solvent whose solubility in water is not larger than 10 wt % and which has a boiling point of from 60° C. to 180° C., thereby obtaining a polyvalent metal salt of said nuclear substituted salicylic acid.

* * * * *